United States Patent
Russinger et al.

(10) Patent No.: US 7,406,148 B2
(45) Date of Patent: Jul. 29, 2008

(54) METHOD FOR IMAGING WITH THE AID OF A MULTIROW COMPUTED TOMOGRAPH

(75) Inventors: Gudrun Russinger, Buckenhof (DE); Johann Russinger, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 109 days.

(21) Appl. No.: 11/297,295

(22) Filed: Dec. 9, 2005

(65) Prior Publication Data
US 2006/0140336 A1 Jun. 29, 2006

(30) Foreign Application Priority Data
Dec. 10, 2004 (DE) .................. 10 2004 059 663

(51) Int. Cl.
*A61B 6/03* (2006.01)
*A61B 6/04* (2006.01)
*H05G 1/62* (2006.01)

(52) U.S. Cl. .................. 378/15; 378/8; 378/95; 600/425; 600/431

(58) Field of Classification Search .......... 378/8, 378/15, 20, 95; 600/425, 431
See application file for complete search history.

(56) References Cited

U.S. PATENT DOCUMENTS

| | | | | |
|---|---|---|---|---|
| 4,941,169 A | * | 7/1990 | Kawai et al. | 378/98.12 |
| 4,995,064 A | * | 2/1991 | Wilson et al. | 378/98.12 |
| 5,150,292 A | * | 9/1992 | Hoffmann et al. | 600/431 |
| 5,347,570 A | | 9/1994 | Haaks | |
| 5,631,942 A | * | 5/1997 | Shinoda | 378/98.12 |
| 5,928,148 A | * | 7/1999 | Wang et al. | 600/420 |
| 6,052,476 A | * | 4/2000 | Qian et al. | 382/130 |
| 6,222,906 B1 | * | 4/2001 | Sakaguchi et al. | 378/98.8 |
| 6,337,992 B1 | * | 1/2002 | Gelman | 600/425 |
| 6,463,121 B1 | * | 10/2002 | Milnes | 378/62 |
| 6,535,821 B2 | * | 3/2003 | Wang et al. | 702/19 |
| 6,637,936 B2 | * | 10/2003 | Crain et al. | 378/197 |
| 6,671,536 B2 | * | 12/2003 | Mistretta | 600/410 |
| 7,313,216 B2 | * | 12/2007 | Nishide et al. | 378/15 |
| 2006/0034419 A1 | * | 2/2006 | Nishide et al. | 378/15 |
| 2006/0109954 A1 | * | 5/2006 | Gohno | 378/98.12 |
| 2006/0178836 A1 | * | 8/2006 | Bai et al. | 702/19 |
| 2006/0233296 A1 | * | 10/2006 | Wakai et al. | 378/8 |

FOREIGN PATENT DOCUMENTS

| | | | |
|---|---|---|---|
| DE | 42 20 282 A1 | | 12/1993 |
| JP | 2004208714 | * | 7/2004 |

* cited by examiner

*Primary Examiner*—Allen C. Ho
(74) *Attorney, Agent, or Firm*—Harness, Dickey & Pierce, P.L.C.

(57) ABSTRACT

A method is for imaging with the aid of a multirow computed tomograph. A volume scan of an examination area of a patient is carried out, with the injection of a contrast medium, at a scanning speed in a scanning direction in order to reconstruct one or more images of the examination area. In the method, the scanning speed is adapted to the propagation speed of the contrast medium in the scanning direction. The method permits the contrast medium requirement to be reduced in the case of CT examinations with the administration of contrast medium.

17 Claims, 3 Drawing Sheets

METHOD FOR IMAGING WITH THE AID OF A MULTIROW COMPUTED TOMOGRAPH

The present application hereby claims priority under 35 U.S.C. §119 on German patent application number DE 10 2004 059 663.8 filed Dec. 10, 2004, the entire contents of which is hereby incorporated herein by reference.

FIELD

The present invention generally relates to a method for imaging with the aid of a multirow computed tomograph. For instance, this can be in the case of which a volume scan of an examination area of a patient is carried out, with the injection of contrast medium, at a scanning speed in one scanning direction in order to reconstruct one or more images of the examination area.

BACKGROUND

Computed tomographs are used in medical imaging for various tasks in order to obtain images of the interior of a body of an examination object. A computed tomograph includes, inter alia, an X-ray tube, X-ray detectors and a patient positioning table. The X-ray tube and the X-ray detectors are arranged on a rotary frame, the so-called gantry, that rotates during the measurement about the patient positioning table or a system axis, the z-axis, running parallel thereto.

The patient positioning table can be moved in this case relative to the gantry along the system axis. The X-ray tube generates an X-ray beam expanded in a slice plane perpendicular to the system axis in a fan-shaped manner. In the case of examinations in the slice plane, this X-ray bundle penetrates a slice of an object, for example a body slice of a patient who is supported on the patient positioning table, and strikes the X-ray detectors situated opposite the X-ray tube. The angle at which the X-ray beam penetrates the body slice of the patient and, if appropriate, the position of the patient positioning table relative to the gantry vary continuously as a rule during the imaging with the aid of the computed tomograph.

The intensity of the X-rays of the X-ray beam that strike the X-ray detectors after penetrating the patient is a function of the attenuation of the X-rays by the patient. Here, each detector element of a detector row of the X-ray detectors generates as a function of the intensity of the received X-radiation a voltage signal that corresponds to a measurement of the global transparency of the body to X-rays from the X-ray tube to the corresponding X-ray detector element. A set of voltage signals of the detector row that correspond to attenuation data and have been recorded for a special position of the X-ray source relative to the patient is noted as a projection. A set of projections that have been recorded at various positions of the gantry during the rotation of the gantry about the patient is denoted as a scan.

The computed tomograph records many projections at various positions of the X-ray source relative to the body of the patient, in order to reconstruct an image that corresponds to a two-dimensional tomographic image of the body of the patient or a three-dimensional image. In order to record a number of tomographic images or a three-dimensional image, a volume scan is carried out that includes a multiplicity of rotations of the gantry in conjunction with a feed movement of the patient table in the z-direction relative to the gantry. The current method for reconstructing a tomographic image or three-dimensional image from recorded attenuation data is known as the method of filtered backprojection.

For many applications of computed tomography (CT), use has already been made nowadays of multislice computed tomographs that facilitate a better exploitation of the generated X-ray emission, as well as faster 3D X-ray pictures. In the case of these units, the X-ray is also conically expanded in the z-direction and therefore covers a larger object volume per recording position of the gantry. A detector array composed of a number of parallel detector rows is used on the side of the examination volume situated opposite the X-ray tube, and so a number of slices of the object can be recorded in each recording position.

As a rule, the CT examination of vessels or vessel structures requires the injection of a contrast medium in order to be able to distinguish the vessels in the recorded images clearly from the surrounding tissue. The contrast medium must be injected in this case over a sufficiently long time period so that there is a higher proportion of contrast medium in the vessels at the instant of recording or acquiring measured data in each slice recorded during the volume scan.

DE 42 20 282 A1 describes a method for recording a number of two-dimensional X-ray projection images after injection of contrast medium in conjunction with a relative displacement between the examination area and the X-ray recording system. For this purpose, the table plate speed is matched to the propagation speed of the contrast medium so that in the ideal case the contrast medium bolus does not change its position in the individual X-ray pictures. In this regard, the document discloses the determination of the contrast medium speed from two adjacent X-ray pictures, the aim being to determine the position of the contrast medium bolus in the X-ray pictures with the aid of a pattern recognition method.

SUMMARY

An object of at least one embodiment of the present invention resides in specifying a method for multidimensional imaging with the aid of a multirow computed tomograph which manages with a reduced quantity of contrast medium for the same image contrast.

In the case of the present method of at least one embodiment, a volume scan of an examination area of a patient is carried out, with the injection of contrast medium, in a scanning direction that corresponds to the opposing feed direction of the patient positioning table of the computed tomograph, in order to reconstruct one or more images of the examination area. The method of at least one embodiment is distinguished in that the scanning speed is matched to the propagation speed of the contrast medium (in the examination area) in the scanning direction.

The time period for the contrast medium injection can be reduced by comparison with the previous mode of procedure by the matching of the scanning speed to the propagation speed of the contrast medium in the scanning direction. The X-ray beam for acquiring measured data in this case moves in the scanning direction together with the contrast medium propagating in the examination volume, that is to say in the vessels of the examination volume, such that there is always a higher proportion of contrast medium in the slice respectively being scanned. The speed at which the X-ray beam sweeps the examination volume in the z-direction in a multirow computed tomograph is higher than the rate of blood flow in this direction, and so to date the contrast medium has had to be injected over a correspondingly long time period.

With the present method of at least one embodiment, the demand for contrast medium in a CT examination with the aid of a multirow computed tomograph can therefore be reduced considerably. The matching of the scanning speed is performed in a way known per se by changing the feed rate of the patient positioning table. The propagation speed of the contrast medium in the scanning direction corresponds to the rate of blood flow in this direction.

In the present method of at least one embodiment, the contrast medium flow is detected locally once or several times as the examination is being carried out. The scanning speed is then matched in each case to the contrast medium flow or the propagation speed determined therefrom. This can be performed once, or else—in the case of a number of measurements of the propagation speed that are offset in time and space—after each individual determination. There is no need in this case to measure the propagation speed itself.

However, it suffices to establish whether there is still sufficient contrast medium present at the instantaneous scanning position or in that section of the examination object currently being X-rayed. If the contrast medium proportion is below a prescribeable threshold value in this section, the scanning speed is varied until a sufficiently high contrast medium proportion is detected again. An optimum matching of the scanning speed to the propagation speed of the contrast medium is achieved in this way during a volume scan in conjunction with sufficiently frequent measurement of the propagation of the contrast medium. The measurement is preferably performed in this case at short intervals of approximately 15-20 mm in the scanning direction. The scanning plane always follows the current contrast medium flow owing to this optimized timing.

The propagation speed or propagation of the contrast medium in the scanning direction can be determined in different ways. Thus, for example, a measuring point can be prescribed as a trigger ROI (Region of Interest) that follows the course of a vessel during the CT examination. This is possible by means of suitable data processing owing to the vessel contrast caused by the contrast medium. The density values are determined at this measuring point during the CT examination with a time offset in order to be able to reduce or increase the scanning speed in the event of a variation that points to a reduced contrast medium content.

In a further refinement, a topogram is used in advance to determine high density values of the different sections of the examination volume that are caused as a rule by bones. During the CT examination, the mean density value of the slice respectively detected at the instantaneous scanning position, or of an area of the slice is calculated at regular intervals from a projection. High density values assigned to this slice that have been determined in advance with the aid of the topogram are subtracted from this mean density value, and so the remaining density value constitutes a measure of the content of contrast medium in the slice at the instantaneous scanning position. In the case of this refinement, as well, a variation in the contrast medium content can be detected, and the scanning speed can be appropriately matched.

Furthermore, the density values of individual slices can be determined at regular intervals by means of a native CT examination previously carried out. These density values are then subtracted, in the same way as for the previous refinement, from the mean density of the slice at the instantaneous scanning position, in order to monitor the instantaneous contrast medium content.

One possibility for the direct determination of the propagating speed of the contrast medium in the scanning direction is offered by the multirow configuration of the detector of a multislice computed tomograph. Thus, directly before the start of the table feed for the volume scan of the CT examination, it is possible to read out the measured values, corresponding to density values, of different detector rows when these are at the start position for the volume scan. By comparing these read out density values of the different detector rows, the arrival time of the contrast medium, and the speed thereof, can be determined. Thus, for example, a starting instant can be set firstly as soon as the first detector row (seen in the scanning direction) detects an increased density value that is above a prescribeable threshold value.

The exceeding of this threshold value means that the contrast medium has arrived at this body position. Proceeding from this starting instant, the time is measured until the threshold value is reached or exceeded at a further detector row (second to nth given n detector rows). This measurement can be performed over the entire detector width (width perpendicular to the scanning direction), but can also be limited to a specific ROI (Region of Interest) in order to increase the sensitivity. This measurement is performed directly before the start of the volume scan, that is to say still without table feed. Since the distance between the individual detector rows is known, the rate of flow of the contrast medium can be determined, and the volume scan can be started at the appropriate scanning speed.

Furthermore, the multirow detector can also be utilized for the real time control of the scanning speed by comparing density or attenuation values of detector rows leading in the scanning direction at a specific body position, that is to say a specific position of the examination area, with the density or attenuation values that are detected directly thereafter at the same body position with the aid of other detector rows. Thus, for example, changes in the rate of flow of the contrast medium can be directly detected by comparing the density or attenuation values of the initial and final rows of the detector with the attenuation values of respective adjacent rows.

By repeating this evaluation at short intervals of the scanning position, it is possible to implement a quasi continuous matching of the scanning speed to a changing rate of flow of the contrast medium. Attenuation differences of the initial rows in relation to the adjacent rows at a specific body position indicate that the scanning speed is too high. Differences in attenuation of the final rows in relation to the adjacent rows at a specific position are a sign of too low a scanning speed. It is possible in this way for the scanning speed to be optimally matched at any time to the flow of contrast medium in the scanning direction.

Owing to the adaptation of the scanning speed to the propagation speed of the contrast medium, at least one embodiment of the present invention permits a minimization of the contrast medium requirement, and thus a lesser contrast medium burden on the patient. A smaller amount of contrast medium simultaneously reduces the examination costs.

BRIEF DESCRIPTION OF THE DRAWINGS

Embodiments of the present invention are explained below once again by way of example with the aid of example embodiments in conjunction with the drawings without limiting the scope of protection provided by the patent claims. In the drawings:

DETAILED DESCRIPTION OF THE EXAMPLE EMBODIMENTS

Figure 1:
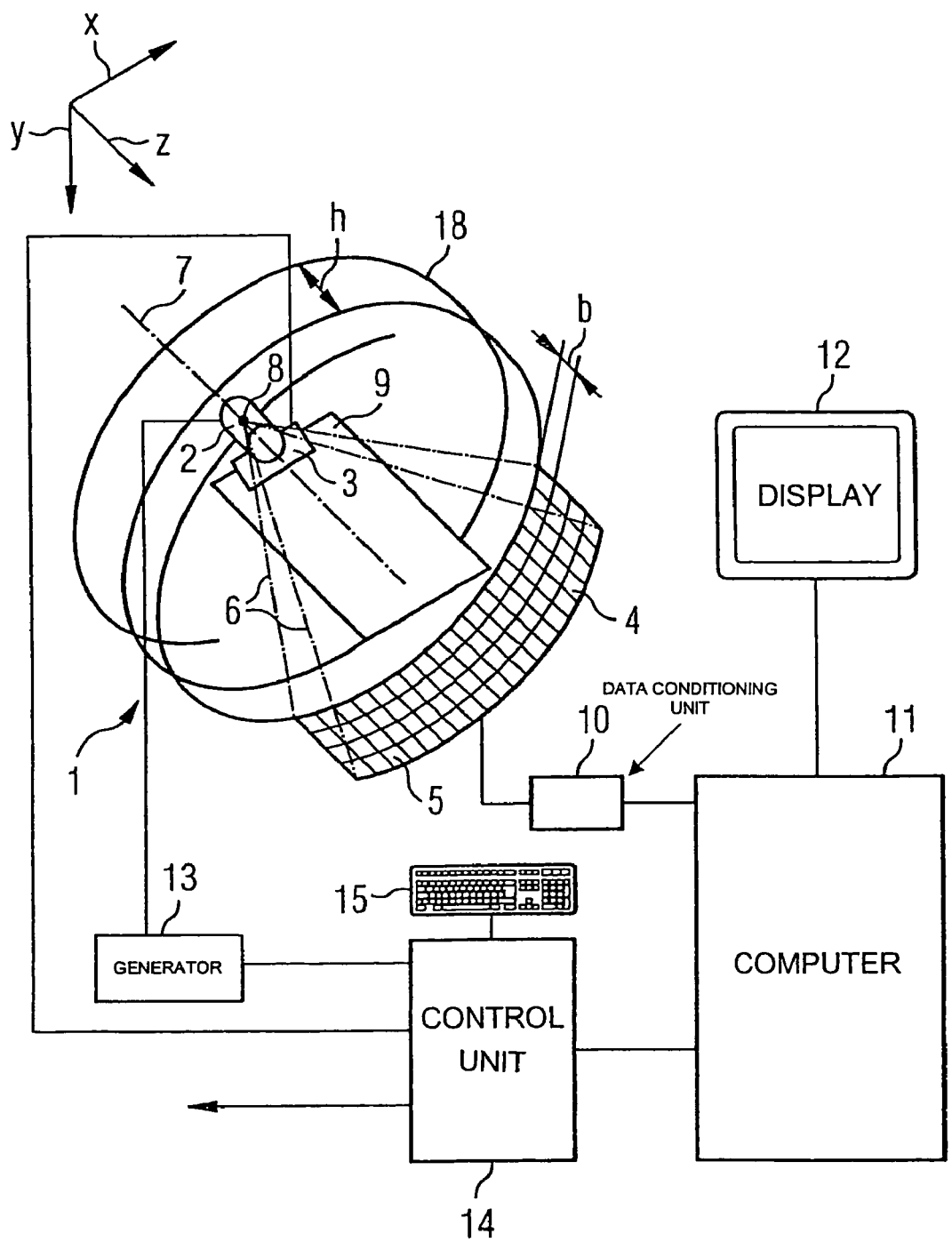
FIG. 1 shows a schematic of a multirow computed tomograph for carrying out at least one embodiment of the present method.

FIG. 1 is a schematic of a multirow computed tomograph 1 with the aid of which it is possible to carry out at least one embodiment of the present method. The measuring arrangement of this computed tomograph 1 includes an X-ray emitter 2 with an insertion device 3 in front thereof and near the source, and an X-ray detector 5 designed as a multirow or planar array of several rows and columns of detector elements 4. For the sake of clarity, only four rows of detector elements 4 are illustrated in the view in FIG. 1. However, the X-ray detector can have further rows of detector elements 4, also with a different width b.

The X-ray emitter 2 with the insertion device 3, on the one hand, and the X-ray detector 5 are fitted on a rotary frame situated opposite one another in such a way that a pyramidal X-ray beam that emanates from the X-ray emitter 2 during operation of the computed tomograph 1 and is inserted by the adjustable insertion device 3, and whose edge rays are designated in FIG. 1 by reference number 6, strikes the X-ray detector 5. The rotary frame can be set in rotation about a system axis 7 by means of a drive device (not shown). The system axis 7 runs parallel to the z-axis of a three-dimensional rectangular coordinate system illustrated in FIG. 1. The columns of the X-ray detector 5 likewise run in the direction of the z-axis, while the rows, whose width b is measured in the direction of the z-axis and is, for example, 1 mm, run transverse to the system axis 7 or the z-axis.

In order to be able to bring the examination object, the patient, into the beam path of the X-ray beam, a patient positioning table 9 is provided that can be displaced parallel to the system axis 7. The displacement is effected in such a way that there is synchronization between the rotation movement of the rotary frame and the translation movement of the patient positioning table 9, it being possible to set the ratio of speed of translation to rotation speed by prescribing a desired value for the feed h of the patient positioning table 9 per revolution of the rotary frame.

An examination volume of an examination object located on the patient positioning table 9 can be examined by volume scanning by operating this computed tomograph 1. In the case of spiral scanning, many projections can be recorded from various projection directions during rotation of the rotary frame and simultaneous translation of the patient positioning table 9 per revolution of the rotary frame. In the case of spiral scanning, the focus 8 of the X-ray emitter 2 moves relative to the patient positioning table 9 on a spiral trajectory 18.

The measured data, which are read out in parallel during spiral scanning from the detector elements 4 of each active row of the detector system 5 and correspond to the individual projections, are subjected to analog-to-digital conversion in a data conditioning unit 10, serialized, and transmitted as raw data to an image computer 11 which displays the result of image reconstruction on the display unit 12, for example a video monitor.

The X-ray emitter 2, for example an X-ray tube, is supplied with the necessary voltages and currents by a generator unit 13. In order to be able to set these to the values respectively required, the generator unit 13 is assigned a control unit 14 with a keyboard 15 which permits the required settings. The remaining operation and control of the computed tomograph 1 is also performed by use of the control unit 14 and the keyboard 15.

The control unit also controls the scanning speed of a volume scan of the computed tomograph by stipulating the feed rate of the patient positioning table 9 and the period of rotation of the rotary frame in accordance with the present method. To this end, the image computer 11, which is connected to the control unit 14, or the control unit 14 comprises a matching module that carries out the evaluation of the attenuation values of the detector rows in order to determine the propagation of the contrast medium in accordance with at least one embodiment of the present method.

Figure 2:
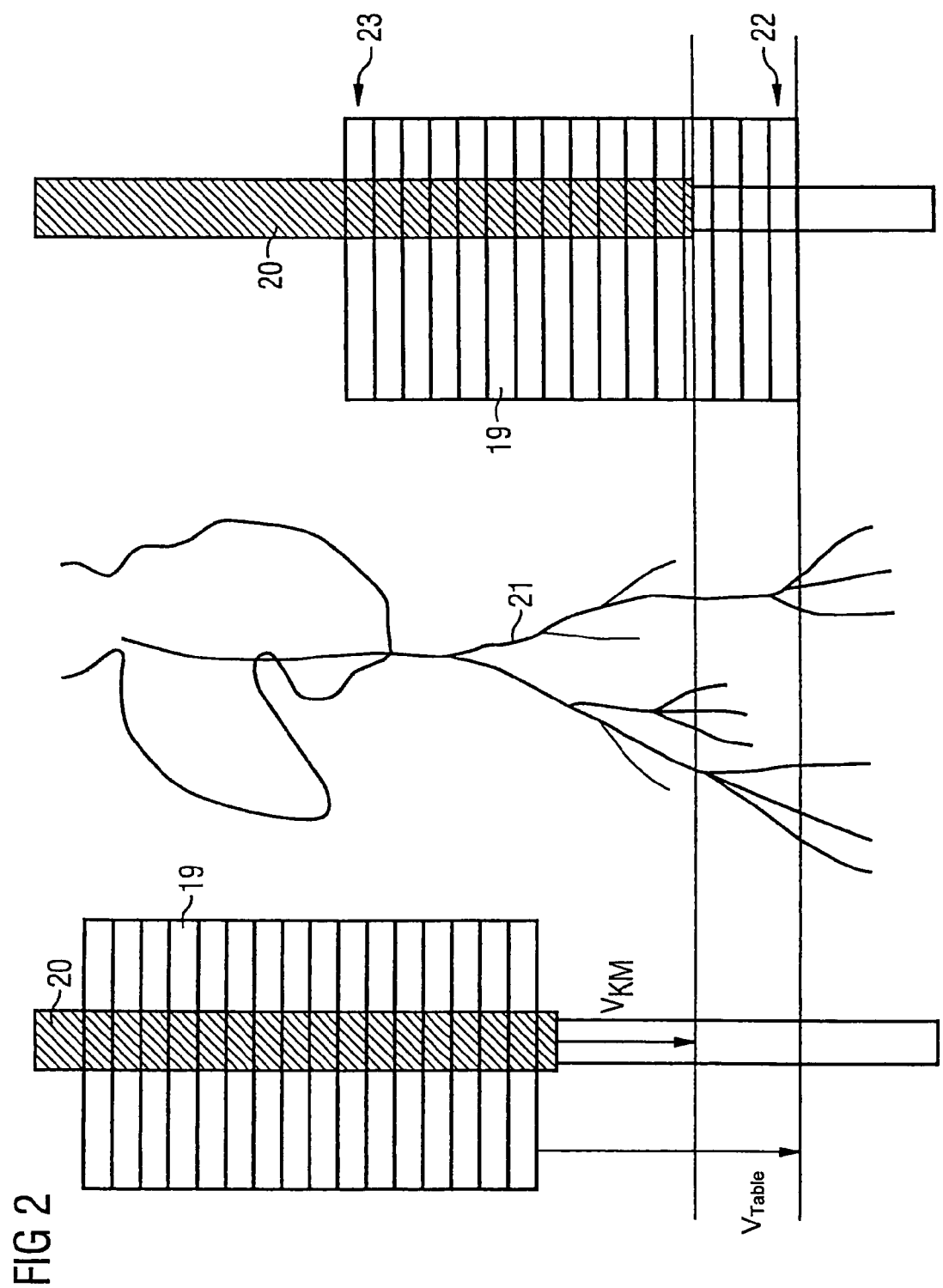
FIG. 2 shows a graphic illustration of the effect of a scanning speed deviating from the propagation speed of the contrast medium.

FIG. 2 shows a graphic representation for the purpose of explaining the effect of a scanning speed that deviates from the propagation speed of the contrast medium in the scanning direction. The example is based on a 16 row computed tomograph. The detector rows 19 each have a width of 1 mm. The table feed therefore corresponds to 16 mm per rotation of the rotary frame.

Visible in the middle of the figure is a vessel system 21 of a patient in the examination area that is currently being scanned. To this end, the left hand part of the figure shows the detector rows 19 moving in the scanning direction, and the section 20, already filled with contrast medium, of the vessel system 21 in the scanning direction, at a first instant. At this instant, the entire examination area detected by the detector rows is filled with contrast medium. The right hand part of the figure shows the conditions at a later, second instant.

In the present example, the table feed $V_{Table}$, which corresponds to the scanning speed $V_s$, is greater than the propagation speed of the contrast medium $v_{KM}$ in the scanning direction. The result of this is that at the second instant the rows of the detector that are at the front in the scanning direction no longer detect an area filled with contrast medium, as is explained in the right hand part of the figure. This mismatch can be detected, for example, by comparing the density values recorded at the same position of the examination area with the aid of the front detector row 22, and (with a time offset) the density values recorded with the aid of the rear detector row 23.

The aim is to match the scanning speed to the propagation speed of the contrast medium in the scanning direction ($v_S=v_{KM}$). In the present example, the table feed is therefore slowed down until the front detector rows are again scanning areas adequately filled with contrast medium.

In the case of a propagation, detected during the carrying out of the CT examination at regular short intervals, of the contrast medium, and corresponding adaptation of the scanning speed at these intervals, it is possible to search an examination area of 100 cm in 21.4 s in conjunction with a small amount of contrast medium and with a collimation of 1.5 mm per row given a 160-row detector. Here, approximately 75 ml of contrast medium are injected at a flow rate of 3.0-3.5 mm/s, followed by an injection of approximately 75 ml NaCl with a flow rate of 3.0-3.5 mm/s. The result of this is an injection period of 21-25 s for the contrast medium.

The arrival time of the contrast medium is measured with the aid of a bolus tracking program (for example CARE Bolus), and the CT examination is started as soon as the contrast medium has arrived in the area to be examined. During the examination, the contrast medium flow is measured at intervals of approximately 15-20 mm. If the measured values are below a threshold value of, for example, 100 HU, the scanning speed is reduced until the measured values are again above the threshold value.

Figure 3:
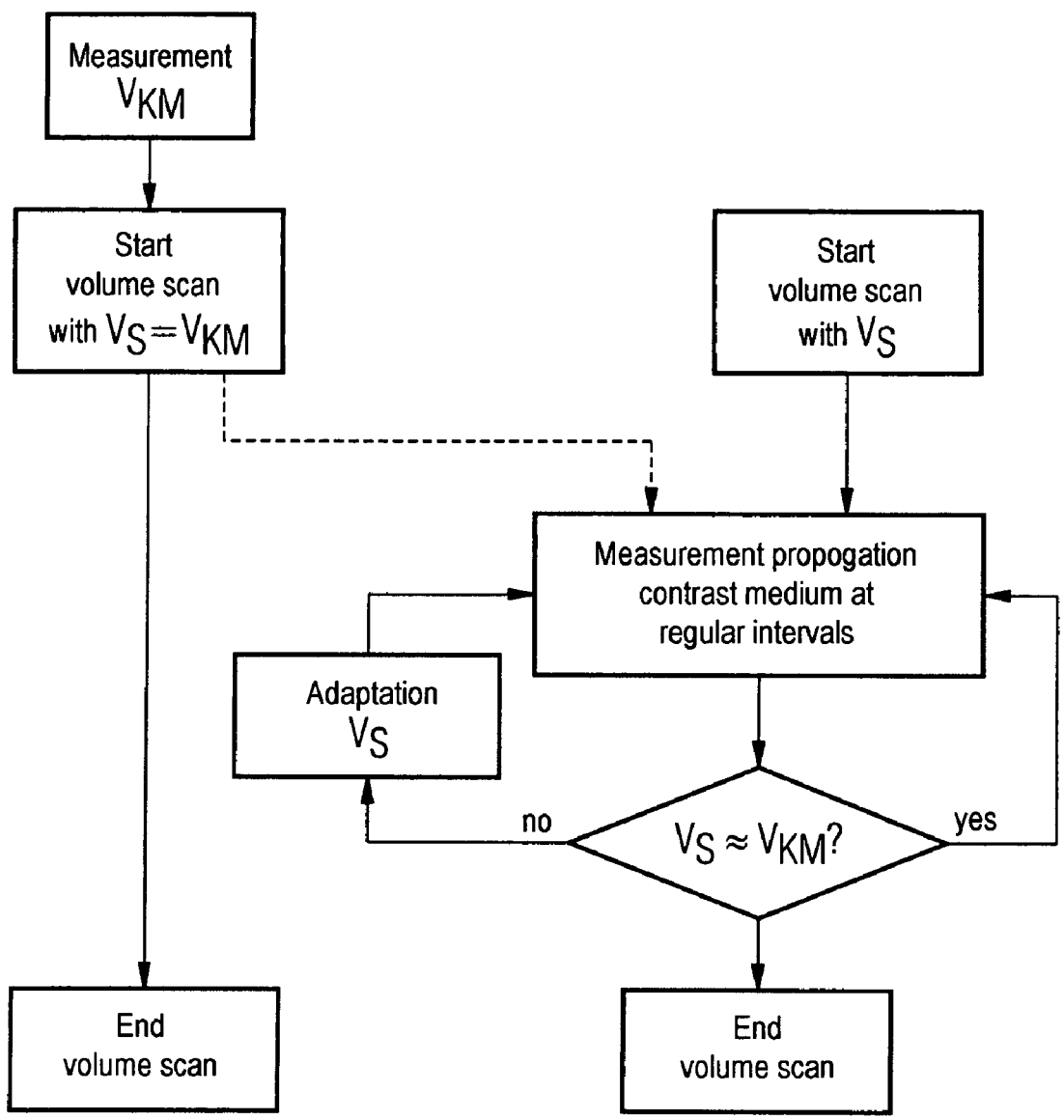
FIG. 3 shows an overview illustration of essential method steps in accordance with an example embodiment of the present method.

The fundamental mode of procedure in carrying out an embodiment of the present method is represented once again by way of example in FIG. 3.

The figure shows an execution of an embodiment of the method in which at specific intervals during the volume scan the propagation of the contrast medium is determined in order to be able to detect and correct any possible deviation of the scanning speed from the propagation speed of the contrast medium. The volume scan can be started in this case on the basis of a fixed scanning speed that can be prescribed by the user or, in accordance with the left-hand part of the figure, by measuring the propagation speed in advance. The repeated determination of the propagation of the contrast medium is performed during the volume scan by reading out and comparing attenuation values of different detector rows at the respective identical position, as has already been explained in more detail in one of the preceding portions of the description.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for multidimensional imaging with the aid of multirow computed tomography in which a volume scan of an examination area of a patient is performed, with an injection of a contrast medium, at a scanning speed in one scanning direction in order to reconstruct one or more images of the examination area, the multirow computed tomography being performed using a multirow detector having a plurality of detector rows, each detector row being composed of several detector elements, the method comprising:

matching the scanning speed to a propagation speed of the contrast medium in the scanning direction the matching including at least one of,
determining a value referring to content of the contrast medium at a respective instantaneous scanning position by reading out and evaluating measured attenuation values from the detector elements of the multirow detector, and if the value referring to the content of the contrast medium drops below a threshold value, at least temporarily reducing or increasing the scanning speed until the value referring to the content of the contrast medium is once again above the threshold value, and
comparing first attenuation values of at least one leading detector row in the scanning direction at an instantaneous position of the detector row with second attenuation values that are detected directly thereafter at the same position with the aid of at least one other detector row, and if a difference between the first and second attenuation values exceeds a threshold value indicative of the arrival of the contrast medium, at least one of reducing and increasing the scanning speed until the difference is below the threshold value; wherein
at least one of the determining step and comparing step is performed repeatedly during the volume scan.

2. The method as claimed in claim 1, wherein, directly before beginning the volume scan at a start position, the method further comprises:
determining an initial propagation speed of the contrast medium in the scanning direction; and
starting the volume scan at a speed corresponding to the initial propagation speed.

3. The method as claimed in claim 2, further comprising:
determining a time after which a rising attenuation value detected at a detector row of the computed tomograph is detected at another detector row of the computed tomograph; and determining the initial propagation speed of the contrast medium at the start position based on the determined time.

4. The method as claimed in claim 3, wherein the value referring to the content of the contrast medium is determined from a mean attenuation value of a number of detector elements of a detector row.

5. The method as claimed in claim 2, wherein the value referring to the content of the contrast medium is determined from a mean attenuation value of a number of detector elements of a detector row.

6. The method of claim 2, wherein in order to determine the initial propagation speed of the contrast medium at the start position, the following steps are performed:
detecting a rising attenuation value based on the propagating contrast medium at a first detector row of the multirow detector;
detecting a rising attenuation value based on the propagating contrast medium at a second detector row of the multirow detector; and
determining a time between the detection of the rising attenuation value at the first detector row and the detection of the rising attenuation value at the second detector row.

7. The method as claimed in claim 1, wherein the value referring to the content of the contrast medium is determined from a mean attenuation value of a number of detector elements of a detector row.

8. A method for matching a scanning speed for scanning an examination area injected with a contrast medium via multirow computed tomography to a propagation speed of the contrast medium in a scanning direction, the multirow computed tomography being performed using a multirow detector having a plurality of detector rows, each detector row being composed of several detector elements, the method comprising at least one of:

determining a value referring to content of the contrast medium at a respective instantaneous scanning position by reading out and evaluating measured attenuation values from the detector elements of the multirow detector, and if the value referring to the contrast medium falls below a threshold value, at least temporarily reducing or increasing the scanning speed until the value referring to the content of the contrast medium is once again above the threshold value; and
comparing first attenuation values of at least one leading detector row in the scanning direction at an instantaneous position of the detector row with second attenuation values that are detected directly thereafter at the same position with the aid of at least one other detector row, and if a difference between the first and second attenuation values exceeds a threshold value indicative of the arrival of the contrast medium, at least one of reducing and increasing the scanning speed until the difference is below the threshold value; wherein
at least one of the determining and comparing is performed repeatedly during the volume scan.

9. The method as claimed in claim 8, wherein, directly before beginning the volume scan at a start position, the method further comprises:
determining an initial propagation speed of the contrast medium in the scanning direction; and
starting the volume scan at a speed corresponding to the initial propagation speed.

10. The method as claimed in claim 9, further comprising:
determining a time after which a rising attenuation value detected at a detector row of the computed tomograph is detected at another detector row of the computed tomograph; and
determining the initial propagation speed of the contrast medium at the start position based on the determined time.

11. The method as claimed in claim 10, wherein the value referring to the content of the contrast medium is determined from a mean attenuation value of a number of detector elements of a detector row.

12. The method as claimed in claim 9, wherein the value referring to the content of the contrast medium is determined from a mean attenuation value of a number of detector elements of a detector row.

13. The method as claimed in claim 8, wherein the value referring to the content of the contrast medium is determined from a mean attenuation value of a number of detector elements of a detector row.

14. A method, comprising:
carrying out a volume scan of an examination area of a patient, with an injection of a contrast medium, at a scanning speed in a scanning direction in order to reconstruct one or more images of the examination area, wherein the scanning speed is matched to a propagation speed of the contrast medium in the scanning direction, the matching including at least one of,
determining a value referring to content of the contrast medium at a respective instantaneous scanning position by reading out and evaluating measured attenuation values from detector elements of a computed tomograph, and if the value referring to the content of the contrast medium falls below a threshold value, at least temporarily reducing or increasing the scanning speed until the value referring to the contrast medium is once again above the threshold value, and
comparing first attenuation values of at least one leading detector row in the scanning direction at an instantaneous position of the detector row with second attenuation values that are detected directly thereafter at the same position with the aid of at least one other detector row, and if a difference between the first and second attenuation values exceeds a threshold value indicative of the arrival of the contrast medium, at least one of reducing and increasing the scanning speed until the difference is below the threshold value.

15. The method as claimed in claim 14, wherein, directly before beginning the volume scan at a start position, the method further comprises:
determining an initial propagation speed of the contrast medium in the scanning direction; and
starting the volume scan at a speed corresponding to the initial propagation speed.

16. The method as claimed in claim 15, further comprising:
determining a time after which a rising attenuation value detected at a detector row of the computed tomograph is detected at another detector row of the computed tomograph; and
determining the initial propagation speed of the contrast medium at the start position based on the determined time.

17. The method as claimed in claim 14, wherein the value referring to the content of the contrast medium is determined from a mean attenuation value of a number of detector elements of a detector row.

* * * * *